United States Patent [19]

Ranken

[11] Patent Number: 4,554,352

[45] Date of Patent: Nov. 19, 1985

[54] PREPARATION OF 1-ALKYL-1,4-DIHYDRO-4-OXO-7-(4-PYRIDYL)-3-QUINOLINECARBOXYLIC ACID

[75] Inventor: Paul F. Ranken, Baton Rouge, La.

[73] Assignee: Ethyl Corporation, Richmond, Va.

[21] Appl. No.: 537,078

[22] Filed: Sep. 29, 1983

[51] Int. Cl.$^4$ .................. C07D 215/16; C07D 211/72; C07D 211/70

[52] U.S. Cl. .................................. 546/156; 546/346; 546/329

[58] Field of Search ............... 546/345, 348, 157, 156, 546/346, 329

[56] References Cited

U.S. PATENT DOCUMENTS 3,753,993  8/1973  Lesher et al. .................. 546/346
3,907,808  9/1975  Lesher et al. .................. 546/346
4,118,557 10/1978  Lesher .......................... 546/346

OTHER PUBLICATIONS

March, Adv. Org. Chem., McGraw-Hill (New York), pp. 482, 484, (1977).
Gordon et al., Jour. of Org. Chem., vol. 29, pp. 329–332, (1964).
Conrow et al., Deductive Organic Chemistry, Addison-Wesley Pub. Co., Inc., Reading, Mass., 1966, p. 182.

Primary Examiner—Henry R. Jiles
Assistant Examiner—Robert C. Whittenbaugh
Attorney, Agent, or Firm—Donald L. Johnson; John F. Sieberth; Patricia J. Hogan

[57] ABSTRACT

4-(Bromophenyl)pyridines, useful in preparing bactericides, are prepared by reacting a 4-phenylpyridine with bromine in the presence of an excess of a Lewis acid catalyst, preferably aluminum chloride.

4 Claims, No Drawings

PREPARATION OF 1-ALKYL-1,4-DIHYDRO-4-OXO-7-(4-PYRIDYL)-3-QUINOLINECARBOXYLIC ACID

FIELD OF THE INVENTION

This invention relates to 4-(bromophenyl)pyridines and more particularly to a process for preparing them.

BACKGROUND

As disclosed in copending applications Ser. No. 300,046 (Walter I), filed Sept. 8, 1981 now U.S. Pat. No. 4,405,792; Ser. No. 495,977 (Walter II), filed May 19, 1983; Ser. No. 497,026 (Ramachandran I) and Ser. No. 497,027 (Ramachandran II), both filed May 23, 1983; and Ser. No. 511,831 (Ramachandran and Ranken), Ser. No. 511,832 (Ramachandran, Ranken, and Wiegand), and Ser. No. 511,913 (Ranken and Ramachandran), all filed July 8, 1983, it is known that 4-(halophenyl)pyridines are useful as intermediates in the preparation of bactericides, such as the 1-alkyl-1,4-dihydro-4-oxo-7-pyridinyl-3-quinolinecarboxylic acids of Sterling Drug's U.S. Pat. Nos. 3,753,993 (Lesher et al.), 3,907,808 (Lesher and Carabateas), and 4,118,557 (Lesher).

Walter I and II, Ramachandran I and II, Ramachandran and Ranken; Ramachandran, Ranken, and Wiegand; and Ranken and Ramachandran all prepare their 4-(halophenyl)pyridines by the aromatization of the corresponding halocyclohexenylpyridines. It would be desirable to be able to prepare them by a technique that would not require an aromatization step.

March, *Advanced Organic Chemistry*, McGraw-Hill (New York), pp. 482–484 (1977), shows that some aromatic compounds can be brominated in the presence of a Lewis acid, and Gordon et al., "The Swamping Catalyst Effect. VI. The Halogenation of Isoquinoline and Quinoline," *Journal of Organic Chemistry*, vol. 29, pp. 329–332 (1964) teaches the effect of the use of an excess of a particular Lewis acid—aluminum chloride—in directing the halogenation of isoquinoline and quinoline.

SUMMARY OF THE INVENTION

An object of this invention is to provide a novel process for preparing 4-(bromophenyl)pyridines.

Another object is to provide such a process requiring no aromatization step.

A further object is to provide processes for preparing derivatives of the 4-(bromophenyl)pyridines.

These and other objects are attained by reacting a 4-phenylpyridine witn bromine in the presence of excess Lewis acid catalyst and, when appropriate, converting the resultant 4-(bromophenyl)pyridine to a desired derivative thereof.

DETAILED DESCRIPTION

4-Phenylpyridines utilizable in the practice of the invention are compounds corresponding to the formula:

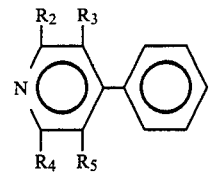

wherein $R_2$, $R_3$, $R_4$, and $R_5$ are independently selected from hydrogen and innocuous substituents, such as alkyl and cycloalkyl, optionally bearing halo substituents and/or optionally joined to the pyridine ring by an ether linkage; halo; cyano; carboxyl; carbalkoxy; carbamyl groups; etc.—any aliphatic groups generally containing 1–6 carbons arranged in straight or branched chains. The preferred 4-phenylpyridine is 4-phenylpyridine itself.

The 4-phenylpyridine is reacted with at least the stoichiometric amount, preferably an excess, of bromine in the presence of an excess of a Lewis acid catalyst, such as aluminum chloride, boron trifluoride, an aluminum alkyl, etc., to prepare the desired products. Desirably, the amount of catalyst employed is in the range of about 1–2 mols per mol of the 4-phenylpyridine. The reaction is conducted in the presence or absence of a suitable solvent, such as nitrobenzene, carbon disulfide, etc.—nonsolvents, such as hexane, 1,2-dichloroethane, etc., being unsuitable alternatives because of their preventing the attainment of the desired bromination. Temperatures suitable for the reaction are generally in the range of about 0°–150° C., e.g., about 70°–95° C.

The process of the invention generally results in the formation of a mixture of o—, m—, and p-brominated 4-phenylpyridines and dibromides which are separable by conventional means when separation is desired. A particularly desired isomer when an intermediate for the aforementioned 1-alkyl-1,4-dihydro-4-oxo-7-pyridinyl-3-quinolinecarboxylic acid bactericides is desired is the 4-(4-bromophenyl)pyridine, which can be converted to the desired bactericide or an intermediate thereof by subjecting it to suitable reactions. These reactions may be conducted by known techniques or, preferably, by the techniques of Walter II, the teachings of which are incorporated herein by reference. Thus, for example:

(1) the 4-(4-bromophenyl)pyridine may be nitrated to a 4-(4-bromo-3-nitrophenyl)pyridine, which may be reduced to a 4-(3-aminophenyl)pyridine, which may be reacted with a dialkyl ethoxymethylenemalonate to form a dialkyl 3-(4-pyridyl)anilinomethylenemalonate, which may be cyclized to an alkyl 1,4-dihydro-4-oxo-7-(4-pyridinyl)-3-quinolinecarboxylate, which in turn may be N-alkylated to an alkyl 1-alkyl-1,4-dihydro-4-oxo-7-(4-pyridinyl)-3-quinolinecarboxylate, which may then be hydrolyzed to a 1-alkyl-1,4-dihydro-4-oxo-7-(4-pyridinyl)-3-quinolinecarboxylic acid, as in Lesher et al. and Lesher and Carabateas, (2) the 4-(4-bromophenyl)pyridine may be nitrated to a 4-(4-bromo-3-nitrophenyl)pyridine, which may be reduced to a 4-(3-aminophenyl)pyridine, which may be reductively alkylated, or acylated and then reduced, as in Lesher, to form a 4-(3alkylaminophenyl)pyridine, otherwise designated as a 3-(4-pyridinyl)-N-alkylaniline, which may then be (a) subjected to the reaction steps of Lesher et al. and Lesher and Carabateas without the need for their N-alkylation step or (b) subjected to reaction with a cyclic alkylidenyl alkoxymethylenemalonate, etc., as in Lesher, to form the antibacterial agent, or (3) either of the above procedures may be terminated at the end of any step to recover a desired product for use in any other desired process, etc.

The following examples are given to illustrate the invention and are not intended as a limitation thereof.

EXAMPLE I

A mixture of one molar proportion of 4-phenylpyridine and 1.2 molar proportions of anhydrous aluminum chloride in 4.9 molar proportions of nitrobenzene was stirred at 85°–95° C. in nitrogen atmosphere to form a gray solution to which 1.2 molar proportions of bromine were added over a period of 30 minutes. The resultant solution was stirred at 85°–95° C. overnight and then poured onto cracked ice. The reaction was worked-up using conventional acidbase partitioning to give the bromide as a semi-solid mass. Gas chromatographic analysis using biphenyl as an internal standard showed that 89% of the 4-phenyl pyridine was reacted to give a 32% yield of 4-(4-bromophenyl)pyridine, a 35% of 4-(3-bromophenyl)pyridine, a 15% yield of 4-(2-bromophenyl)pyridine, and a 14% yield of dibromides. Recrystallization of the mass from n-hexane gave 4-(4-bromophenyl)pyridine as beautiful white needles, m.p. 127-9; pure by gc and nmr analyses.

EXAMPLE II

Example I was essentially repeated except that the bromination was conducted in the absence of a solvent. The process resulted in a 31% yield of 4-(4-bromophenyl)pyridine, a 31% yield of 4-(3-bromophenyl)pyridine, and a 1% yield of 4-(2-bromophenyl)pyridine.

COMPARATIVE EXAMPLE

Two experiments were conducted by repeating Example I except that hexane and 1,2-dichloroethane, respectively, were substituted for the nitrobenzene. No brominated product was obtained in either experiment.

It is obvious that many variations may be made in the products and processes set forth above without departing from the spirit and scope of this invention.

I claim:

1. A process which comprises:
   (a) reacting a 4-phenylpyridine with bromine in the presence of excess Lewis acid catalyst to form a 4-(4-bromophenyl)pyridine,
   (b) nitrating the 4-(4-bromophenyl)pyridine to a 4-(4-bromo-3-nitrophenyl)pyridine,
   (c) reducing the 4-(4-bromo-3-nitrophenyl)pyridine to a 4-(3-aminophenyl)pyridine,
   (d) reacting the 4-(3-aminophenyl)pyridine with a dialkyl ethoxymethylenemalonate to form a dialkyl 3-(4-pyridinyl)-anilinomethylenemalonate,
   (e) cyclizing the dialkyl 3-(4-pyridinyl)anilinomethylenemalonate to an alkyl 1,4-dihydro-4-oxo-7-(4-pyridinyl)-3-quinolinecarboxylate,
   (f) N-alkylating the alkyl 1,4-dihydro-4-oxo-7-(4-pyridinyl)-3-quinolinecarboxylate to an alkyl 1-alkyl-1,4-dihydro-4-oxo-7-(4-pyridinyl)-3-quinolinecarboxylate, and
   (g) hydrolyzing the alkyl 1-alkyl-1,4-dihydro-4-oxo-7-(4-pyridinyl)-3-quinolinecarboxylate to a 1-alkyl-1,4-dihyro-4-oxo-7-(4-pyridinyl)-3-quinolinecarboxylic acid.

2. The process of claim 1 wherein the 4-phenylpyridine is 4-phenylpyridine, the Lewis acid is aluminum chloride, and the Lewis acid catalyst is employed so as to provide about 1–2 molar proportions of catalyst per molar proportion of the 4-phenylpyridine.

3. A process which comprises:
   (a) reacting a 4-phenylpyridine with bromine in the presence of excess Lewis acid catalyst to form a 4-(4-bromophenyl)pyridine,
   (b) nitrating the 4-(4-bromophenylpyridine to a 4-(4-bromo-3-nitrophenyl)pyridine,
   (c) reducing the 4-(4-bromo-3-nitrophenyl)pyridine to a 4-(3-aminophenyl)pyridine,
   (d) converting the 4-(3-aminophenyl)pyridine to a 3-(4pyridinyl)-N-alkylaniline,
   (e) reacting the 3-(4-pyridinyl)-N-alkylaniline with a dialkyl ethoxymethylenemalonate to form a dialkyl 3-(4-pyridinyl)-N-alkylanilinomethylenemalonate,
   (f) cyclizing the dialkyl 3-(4-pyridinyl)-N-alkylanilinomethylenemalonate to an alkyl 1-alkyl-1,4-dihydro-4-oxo-7-(4-pyridinyl)-3-quinolinecarboxylate, and
   (g) hydrolyzing the alkyl 1-alkyl-1,4-dihydro-4-oxo-7-(4-pyridinyl)-3-quinolinecarboxylate to a 1-alkyl-1,4-dihydro-4-oxo-7-(4-pyridinyl)-3-quinolinecarboxylic acid.

4. The process of claim 3 wherein the 4-phenylpyridine is 4-phenylpyridine, the Lewis acid is aluminum chloride, and the Lewis acid catalyst is employed so as to provide about 1–2 molar proportions of catalyst per molar proportion of the 4-phenylpyridine.

* * * * *